United States Patent [19]

Gupta et al.

[11] Patent Number: 4,929,789
[45] Date of Patent: May 29, 1990

[54] PROCESS FOR PYROLYZING OR THERMAL CRACKING A GASEOUS OR VAPORIZED HYDROCARBON FEEDSTOCK USING A NOVEL GAS-SOLIDS CONTACTING DEVICE AND AN OXIDATION CATALYST

[75] Inventors: Victor R. Gupta, Cleveland Hts.; Christopher J. Clark, Aurora, both of Ohio

[73] Assignee: The Standard Oil Company, Cleveland, Ohio

[21] Appl. No.: 144,545

[22] Filed: Jan. 15, 1988

[51] Int. Cl.$^5$ .................................................. C07C 4/04
[52] U.S. Cl. ...................... 585/648; 585/649; 585/650; 431/7; 208/48 Q; 208/100; 208/127; 208/129; 208/130; 422/145
[58] Field of Search ............... 208/106, 130, 127, 125, 208/48 Q, 100; 585/650, 651, 648, 652, 653, 539, 540, 541; 422/145

[56] References Cited

U.S. PATENT DOCUMENTS

| 1,656,813 | 1/1928 | Bird | 585/416 |
| 1,863,212 | 6/1932 | Winkler | 585/415 |
| 1,922,918 | 8/1933 | Winkler et al. | 260/168 |

(List continued on next page.)

FOREIGN PATENT DOCUMENTS

| 0189079 | 7/1986 | European Pat. Off. | 585/415 |
| 8500141 | 7/1985 | PCT Int'l Appl. | 585/709 |
| 2148933 | 6/1986 | United Kingdom | 585/652 |
| 2148935 | 6/1986 | United Kingdom | 585/652 |

OTHER PUBLICATIONS

Dodson, C. E., "The Torbed Process, an Overview", Presented at 7th Industrial Minerals International Congress, Monte Carlo, Apr. 1986 and Published in Industrial Minerals Jul., 1986 Supplement, Industrial Minerals Processing: Some Recent Developments.
Torftech Ltd. (No. 1), "The Torbed Process", Product Literature Distributed by Torftech Ltd., Mortimer Hill, Mortimer, Reading, Berkshire RG73PG, United Kingdom.

(List continued on next page.)

Primary Examiner—Anthony McFarlane
Attorney, Agent, or Firm—Raymond F. Keller; David J. Untener; Larry W. Evans

[57] ABSTRACT

A process is disclosed for converting a gaseous or vaporized hydrocarbon feedstock to a product comprising ethylene, acetylene or a mixture thereof. The process comprises the steps of advancing a gaseous or vaporized stream comprising a gaseous or vaporized fuel and an oxygen source into contact with particulate solids in one section of an annular gas-solids contacting zone, said stream being deflected at the entrance to said one section of said contacting zone sufficiently to move said solids in a generally circumferential and horizontal direction, said particulate solids being at a sufficiently high temperature to effect combustion of said gaseous fuel, said particulate solids comprising an effective amount of at least one oxidation catalyst to enhance the combustion of said fuel, combusting said gaseous fuel, the heat from said combustion heating said solids, and removing a gaseous or vaporous material comprising exhaust gases or vapors from said combustion from said one section of said contacting zone; moving said particulate solids to another section of said contacting zone, the movement of said solids being effected by the flow of said gaseous stream, advancing said feedstock into said another section of said annular contacting zone into contact with said particulate solids, said feedstock being deflected at the entrance to said another section of said contacting zone sufficiently to move said solids in a generally circumferential and horizontal direction, converting at least some of said feedstock to said product, and removing said product from said another section of said contacting zone; and returning said particulate solids to said one section of said contacting zone. The resulting product can then be converted to higher order hydrocarbons, especially substantially liquid hydrocarbons.

29 Claims, 3 Drawing Sheets

U.S. PATENT DOCUMENTS

| | | | |
|---|---|---|---|
| 1,945,960 | 2/1934 | Winkler et al. | 260/170 |
| 1,988,873 | 1/1935 | Linckh et al. | 260/168 |
| 2,436,595 | 2/1948 | Nicholson et al. | 260/666 |
| 2,679,544 | 5/1954 | Bills | 260/679 |
| 2,859,258 | 11/1958 | Fischer et al. | 260/683 |
| 3,093,697 | 6/1963 | Kasbohm et al. | 260/679 |
| 3,156,733 | 11/1964 | Happel et al. | 260/679 |
| 3,234,300 | 2/1966 | Howard | 260/679 |
| 3,244,765 | 4/1966 | Fauser | 260/679 |
| 3,248,447 | 4/1966 | Lorenz et al. | 260/679 |
| 3,452,114 | 6/1969 | Friz et al. | 260/679 |
| 4,044,117 | 8/1977 | Matovich | 208/106 |
| 4,051,014 | 9/1977 | Masologites | 208/131 |
| 4,061,562 | 12/1977 | McKinney et al. | 208/61 |
| 4,100,218 | 7/1978 | Chen et al. | 260/673 |
| 4,120,910 | 10/1978 | Chu | 260/673 |
| 4,142,963 | 3/1979 | Kearns | 208/130 |
| 4,176,045 | 11/1979 | Leftis et al. | 208/48 R |
| 4,256,565 | 3/1981 | Friedman et al. | 585/650 |
| 4,259,177 | 3/1981 | Ueda et al. | 585/650 |
| 4,349,432 | 9/1982 | Rowe et al. | 208/130 |
| 4,433,192 | 2/1984 | Olah | 585/709 |
| 4,443,645 | 4/1984 | Jones et al. | 585/500 |
| 4,479,869 | 10/1984 | Petterson et al. | 208/130 |
| 4,479,920 | 10/1984 | Dodson | 422/143 |
| 4,489,215 | 12/1984 | Withers | 585/500 |
| 4,495,374 | 1/1985 | Jones | 585/500 |
| 4,507,517 | 3/1985 | Devries et al. | 585/415 |
| 4,513,164 | 4/1985 | Olah | 585/700 |
| 4,520,217 | 5/1985 | Minet et al. | 585/415 |
| 4,556,749 | 12/1985 | Harlon | 585/330 |
| 4,559,719 | 12/1985 | Dodson | 34/10 |
| 4,560,821 | 12/1985 | Jones et al. | 585/500 |
| 4,655,904 | 4/1987 | Okamoto et al. | 208/129 |
| 4,658,081 | 4/1987 | Kolts | 585/653 |
| 4,675,098 | 6/1987 | Miyauchi et al. | 208/127 |
| 4,687,642 | 8/1987 | Nielsen | 208/127 |
| 4,705,908 | 11/1987 | Gondouin | 585/500 |

OTHER PUBLICATIONS

Torftech Ltd. (No. 2), "The Torbed Process: Food Processing", Product Literature Distributed by Torftech Ltd., Mortimer Hill, Mortimer, Reading, Berkshire RG73PG, United Kingdom.

Torftech Ltd. (No. 3), "The Torbed Process: Mineral Processing", Product Literature Distributed by Torftech Ltd., Mortimer Hill, Mortimer, Reading, Berkshire RG73PG, United Kingdom.

Stanley, H. M., et al, "The Production of Gaseous, Liquid, and Solid Hydrocarbons from Methane, Part I—The Thermal Decomposition of Methane", Transactions, Journa of the Society of Chemical Industry, Jan. 11, 1929, vol. 48, pp. 1–8.

Fischer, F. et al, "The Synthesis of Benzene Hydrocarbons from Methane at Normal Pressure and Without a Catalyst", Brennstoff-Chemie, vol. 9, No. 19, pp. 309–324 (1928), Kaiser Wilhelm Coal Research Institute, Mulheim-Ruhr.

Smith, H. M., et al, "Production of Motor Fuels from Natural Gas—I. Preliminary Report on the Pyrolysis of Methane", Report of Investigations, Department of Commerce—Bureau of Mines, R.I.3143, Oct., 1931.

Chemical Economy and Engineering Review, Jul.-/Aug. 1985, vol. 17, No. 7.8 (No. 190), pp. 47–48.

PROCESS FOR PYROLYZING OR THERMAL CRACKING A GASEOUS OR VAPORIZED HYDROCARBON FEEDSTOCK USING A NOVEL GAS-SOLIDS CONTACTING DEVICE AND AN OXIDATION CATALYST

TECHNICAL FIELD

This invention relates to a process for pyrolyzing or thermal cracking a gaseous or vaporized hydrocarbon feedstock using a novel gas-solids contacting device and a novel oxidation catalyst. More particularly this invention relates to a process for converting a gaseous or vaporized hydrocarbon feedstock to a product comprising ethylene, acetylene or a mixture thereof. The invention also relates to the conversion of said product to higher order hydrocarbons, especially substantially liquid hydrocarbons. A novel gas-solids contacting device is used to effect a rapid transfer of heat to the feedstock. An oxidation catalyst is used to effect rapid and complete combustion of the gaseous fuel used for heating. The process is particularly suitable for converting methane and/or natural gas to a product comprising ethylene and/or acetylene, and, optionally, converting said product to higher order hydrocarbons.

BACKGROUND OF THE INVENTION

The term "higher order hydrocarbon" refers to a hydrocarbon product having at least one more carbon atom in its structure than the hydrocarbon used in the reactant to form said higher order hydrocarbon. For example, if the reactant comprised methane, and ethane was formed from said reactant, ethane would be a higher order hydrocarbon. The term "substantially liquid hydrocarbon" refers to hydrocarbons that are substantially in the liquid form at a temperature of about 25° C. and a pressure of one atmosphere.

The production of acetylene by the cracking of petroleum hydrocarbons with steam or the partial oxidation of natural gas is known. The production of ethylene by the thermal cracking of ethane, propane, butane, naphtha and refinery off-gases is known.

U.S. Pat. No. 3,093,697 discloses a process for making acetylene by heating a mixture of hydrogen and a hydrocarbon stock (e.g., methane) at a reaction temperature that is dependent upon the particular hydrocarbon employed for about 0.01 to 0.05 second. The reference indicates that a reaction temperature of 2700° F. (1482° C.) to 2800° F. (1538° C.) is preferred for methane and that lower temperatures are preferred for higher molecular weight hydrocarbons.

U.S. Pat. No. 3,156,733 discloses a process for the pyrolysis of methane to acetylene and hydrogen. The process involves heating a methane-containing stream in a pyrolytic reaction zone at a maximum temperature above 1500° C. and sequentially withdrawing a gaseous product from said reaction zone and quenching said product rapidly to a temperature of about 600° C. or less.

U.S. Pat. No. 4,176,045 discloses a process for the production of olefins by steam-cracking normally liquid hydrocarbons in a tubular reactor wherein the residence time in the tubes is from about 0.02 to about 0.2 second and the formation of coke deposits in the tubular reactor is minimized.

Chemical Economy and Engineering Review, July/August 1985, Vol. 17, No. 7.8 (No. 190), pp. 47-48, discloses that furnaces have been developed commercially for steam cracking a wide range of liquid hydrocarbon feedstocks using process reaction times in the range of 0.05 to 0.1 second. This publication indicates that the use of these furnaces permits substantial increases in the yield of olefins (i.e., ethylene, propylene, butadiene) while decreasing production of less-desirable co-products.

Natural gas typically contains about 40-95% methane depending on the particular source. Other constituents include about 10% of ethane with the balance being made up of $CO_2$ and smaller amounts of propane, the butanes, the pentanes, nitrogen, etc. Primary sources for natural gas are the porous reservoirs generally associated with crude oil reserves. From these sources come most of the natural gas used for heating purposes. Quantities of natural gas are also known to be present in coal deposits and are by-products of crude oil refinery processes and bacterial decomposition of organic matter. Prior to commercial use, natural gas must be processed to remove water vapor, condensible hydrocarbons and inert or poisonous constituents. Condensible hydrocarbons are generally removed by cooling natural gas to a low temperature and then washing the natural gas with a cold hydrocarbon liquid to absorb the condensible hydrocarbons. The condensible hydrocarbons are typically ethane and heavier hydrocarbons. This gas processing can occur at the wellhead or at a central processing station. Processed natural gas typically comprises a major amount of methane, and minor amounts of ethane, propane, the butanes, the pentanes, carbon dioxide and nitrogen. Generally, processed natural gas comprises from about 70% to more than about 95% by volume of methane. Natural gas is used principally as a source of heat in residential, commercial and industrial service.

Most processed natural gas is distributed through extensive pipeline distribution networks. As natural gas reserves in close proximity to gas usage decrease, new sources that are more distant require additional transportation. Many of these distant sources are not, however, amenable to transport by pipeline. For example, sources that are located in areas requiring economically unfeasible pipeline networks or in areas requiring transport across large bodies of water are not amendable to transport by pipeline. This problem has been addressed in several ways.

One approach has been to build a production facility at the site of the natural gas deposit to manufacture one specific product. This approach is limited as the natural gas can be used only for one product, preempting other feasible uses. Another approach has been to liquefy the natural gas using cryogenic techniques and transport the liquid natural gas in specially designed tanker ships. Natural gas can be reduced to 1/600th of the volume occupied in the gaseous state by such cryogenic processing, and with proper procedures, safely stored or transported. These processes, which involve liquefying natural gas to a temperature of about −162° C., transporting the gas, and revaporizing it are complex and energy intensive.

Still another approach involves the use of pyrolysis to convert the natural gas to higher order hydrocarbons (e.g., substantially liquid hydrocarbons) that can be easily handled and transported. Low temperature pyrolysis (e.g., to 250° C. and 500° C.) is described in U.S. Pat. Nos. 4,433,192; 4,497,970; and 4,513,164. The processes described in these patents utilize heterogeneous systems and solid acid catalysts. In addition to the solid acid catalysts, the reaction mixtures described in the '970 and '164 patents include oxidizing agents. Among the oxidizing agents disclosed are air, $O_2$-$O_3$ mixtures, S, Se, $SO_3$, $N_2O$, NO, $NO_3$, F, etc. The conversion of natural gas to higher order hydrocarbons at higher temperatures (e.g., above about 1200° C.) using pyrolysis has been suggested. These high-temperature processes are, however, energy intensive and have thus far not been developed to the point where high yields are obtained even with the use of catalysts. Some catalysts that are useful in these processes (e.g., chlorine) are corrosive under such operating conditions.

A common technique for pyrolyzing natural gas involves the use of tubular reactors. The natural gas flows through a tube placed inside a radiant and/or convective chamber of a furnace. The heat supplied to the natural gas is dependent upon the surface area of the tubes, and thus only relatively small diameter tubes are typically used. When using such tubular reactors in the pyrolysis of natural gas, coke tends to build up on the inner walls of the tubes. Because of the small diameter of the tubes, any deposited coke forms a relatively thick layer and thereby severely inhibits further heat transfer. Tubular reactors can be used for cracking hydrocarbons like ethane or propane due to the fact that hydrocarbons of this type do not produce significant levels of coke. However, the amount of coke produced during pyrolysis of natural gas is substantially greater and thus tubular reactors cannot be operated continually for more than a few minutes or a few hours at a time. The use of tubular reactors for the pyrolysis of natural gas is also restricted by the materials available for making the tubes. Typically these reactors have maximum operating temperatures of only about 1050° C. due to the materials of construction used in the tubes, while on the other hand significantly improved yields in the pyrolysis of natural gas could be achieved if higher operating temperatures could be used.

Riser reactors of the type disclosed in U.S. Pat. No. 4,061,562 have been suggested for thermal cracking of petroleum oils. A mixture of hot solids (e.g., non-catalytic alumina, alundum, carborundum, coke, etc.), feed oil (e.g., hydrodesulfurized residual petroleum oil) and gaseous diluent (e.g., steam) flow co-currently through a thermariser at an average riser temperature of 1300° F. to 2500° F. (704° C. to 1371° C.) to produce hydrocarbon products. The hydrocarbon products obtained by this process include ethane, ethylene, propylene, 1,3-butadiene, other $C_4$ hydrocarbons, benzene, toluene, xylene, liquids boiling in the gasoline range, and light and heavy gas oils. This patent indicates that during the process coke forms on the solids and is carried out of the reactor with such solids thus limiting harmful build-up of coke on the reactor walls. A disadvantage with these riser reactors is that due to the co-current flow of the solids and gases, such solids and gases must be separated by an external cyclone. Also, the product gases can only be quenched after separating the solids, otherwise the process would be thermally inefficient. Another disadvantage is that it is not possible to use relatively short residence times (e.g., below about 50 milliseconds) and thus the use of these reactors for pyrolyzing feedstocks such as natural gas is severely limited.

Fluidized beds typically comprise a processing chamber which is partially filled with particulate solids. The floor of the chamber constitutes a perforated plate and, in use, a gas is forced up through this plate. The particulate solids in the chamber are agitated sufficiently so as to form a turbulent mass resembling a boiling liquid. This is the "fluidized bed". Heating of the fluidized bed can be effected by combustion of the gas below the plate before it enters the chamber, or by internal combustion of the gas within the bed. In theory, the fluidized bed provides an effective transfer mechanism which offers benefits in a variety of thermal and/or catalytic processing systems. In practice, however, the use of fluidized beds has been limited when relatively high heat and/or mass transfer rates have been desired due to, among other things, undesirable entrainment of the solid particles out of the fluidized bed. As the demand for higher heat and/or mass transfer rates has evolved, means have been sought to increase the performance of fluidized bed processes. This has usually led to the use of higher fluidizing velocities resulting in the use of "entrained beds". The use of entrained beds has not, however, been entirely satisfactory. One of the problems with the use of such entrained beds relates to the inherent problems involved with recovering and recirculating entrained particulate solids.

U.S. Pat. Nos. 4,479,920 and 4,559,719 disclose an apparatus and process for processing matter in a turbulent mass of particulate material in a substantially annular processing region. These patents indicate that the processing region is preferably in the form of a substantially annular processing chamber having a radially inner wall which includes a waist. A flow of fluid and particulate material to be processed are admitted to the processing region through one or more inlets with the flow of fluid being directed generally circumferentially into the processing region. In the processing region, particulate material to be processed is embedded in a compact turbulent band. Once processing is complete, the processed matter is withdrawn from the processing region, preferably by entrainment in an exhaust flow of the fluid.

Combustion is an exothermic oxidation reaction in which the heat evolved results from the formation of carbon oxygen bonds. For each carbonaceous material there is a specific carbon to oxygen ratio that ideally corresponds to complete or stoichiometric combustion. The terms "complete combustion" and "stoichiometric combustion" are used herein to refer to the conversion of a carbonaceous material to $CO_2$ with no CO being produced. Complete combustion is often desirable because the production of heat is maximized and the production of pollutants (e.g., carbon monoxide) is eliminated. Complete or stoichiometric combustion of methane, acetylene, ethylene, ethane, propane, butane and benzene can be represented by the following equations:

$$CH_4 + 2O_2 = CO_2 + 2H_2O$$

$$C_2H_2 + 2.5O_2 = 2CO_2 + H_2O$$

$$C_2H_4 + 3O_2 = 2CO_2 + 2H_2O$$

$$C_2H_6 + 3.5O_2 = 2CO_2 + 3H_2O$$

$$C_3H_8 + 5O_2 = 3CO_2 + 4H_2O$$

$$C_4H_{10} + 6.5O_2 = 4CO_2 + 5H_2O$$

$$C_6H_6 + 7.5O_2 = 6CO_2 + 3H_2O$$

In the above equations, 2 moles of oxygen are required per mole of methane to achieve complete or stoichiometric combustion of methane; 2.5 moles of oxygen are needed per mole of acetylene to achieve complete or stoichiometric combustion of acetylene; 3 moles of oxygen per mole of ethylene are needed to achieve complete or stoichiometric combustion of ethylene; etc. Similar equations can be used to represent the complete or stoichiometric combustion of other carbonaceous materials. The amount of air required for a stoichiometric mixture for many carbonaceous fuels is provided in Perry, J. H., et al, Editors, "Chemical Engineer's Handbook", Fourth Edition (1963) at pp. 9-31 to 9-33.

In large-scale or commercial operations involving the combustion of carbonaceous fuels, it is usually not possible to obtain complete combustion with only a stoichiometric amount of oxygen or air. It is thus common practice to add excess oxygen or air (that is, oxygen or air in excess of stoichiometric amount required to provide complete combustion) to effect complete or substantially complete combustion. The amount of excess oxygen or air required depends on many factors including the particular carbonaceous fuel being burned, the type of burner or furnace being used, etc. Adding excess oxygen or air has certain disadvantages. The excess oxygen or air decreases the efficiency of the combustion process by reducing its ultimate obtainable temperature and by increasing the size of the equipment necessary to convert all of the carbonaceous fuel to carbon dioxide. The use of oxidation catalysts to enhance combustion and thereby eliminate the requirement for excess oxygen or air has been suggested.

U.S. Pat. Nos. 3,926,854 and 3,947,380 disclose ceramic mixed oxide, non-stoichiometric electrically neutral rare-earth-type catalysts containing rare-earth—type elements and elements of the first transition metal series and optionally alkaline earth metals. These catalysts have the following formula:

$$X_n J(1-n) ZO(3+m)$$

wherein: X is an alkaline earth metal or mixture thereof; J is a rare-earth-type element or mixture thereof; Z is a metal of the first transition series or a mixture thereof, at least 0.01% of said metal having an oxidation state other than +3; m is a number having a value of between zero and about 0.11; and n is a number having a value from zero to about 0.51. These patents indicated that these catalysts can be used to catalytically oxidize low molecular weight inorganic compounds and elements, such as ammonia, carbon monoxide, hydrogen, sulfur dioxide, and hydrogen sulfide, with oxygen, or carbon monoxide with water, sulfur dioxide or nitric oxide. The catalyst can also be employed in the catalytic removal of carbon monoxide, hydrocarbons and nitric oxides from the exhaust gases of generating or heating plants and automobiles burning fossil fuels.

U.S. Pat. Nos. 3,885,020; 3,976,599; 4,076,486; 4,124,689; and 4,124,697 disclose ceramic mixed oxide, non-stoichiometric electrically neutral, rare-earth-type catalysts containing rare-earth-type elements, elements of the first transition metal series and zirconium, tin or thorium and optionally alkaline earth metals. These catalysts have the following formula:

$$W_k X_n J(1-k-n) ZO(3+m)$$

wherein: W is zirconium, tin or thorium or mixture thereof; X is an alkaline earth metal or mixture thereof; J is a rare-earth-type element or mixture thereof; Z is a metal of the first transition series or a mixture thereof, at least 0.01% of said metal having an oxidation state other than +3; k is a number having a value of between zero and about 0.1; m is a number having a value of from zero to about 0.26, provided m has a value other than zero when n has a value of zero; and n is a number having a value from 0 to about 0.51 provided when n has a value of zero, k has a value of between zero and about 0.05. These patents indicate that these catalysts can be used to catalytically oxidize organic compounds to various states of oxidation, ammonia, carbon monoxide, hydrogen, sulfur dioxide, and hydrogen sulfide, with oxygen, or carbon monoxide with water, sulfur dioxide or nitric oxide. The catalyst can also be employed in the catalytic removal of carbon monoxide, hydrocarbons, nitric oxides and sulfur dioxide from the exhaust gases of generating or heating plants and automobiles burning fossil fuels. In addition, these catalysts can be employed to produce hydrogen cyanide from methane, ammonia and oxygen.

SUMMARY OF THE INVENTION

The present invention provides for a process for converting a gaseous or vaporized hydrocarbon feedstock to a product comprising ethylene, acetylene or a mixture thereof, and, optionally converting said product to higher order hydrocarbons, especially substantially liquid hydrocarbons. The process comprises the steps of advancing a gaseous or vaporized stream comprising a gaseous or vaporized fuel and an oxygen source into contact with particulate solids in one section of an annular gas-solids contacting zone, said stream being deflected at the entrance to said one section of said contacting zone sufficiently to move said solids in a generally circumferential and horizontal direction, said particulate solids being at a sufficiently high temperature to effect combustion of said fuel, said particulate solids comprising an effective amount of at least one oxidation catalyst to enhance the combustion of said fuel, combusting said fuel, the heat from said combustion heating said solids, and removing a gaseous or vaporous material comprising exhaust gases or vapors from said combustion from said one section of said contacting zone; moving said particulate solids to another section of said contacting zone, the movement of said solids being effected by the flow of said stream; advancing said feedstock into said another section of said annular contacting zone into contact with said particulate solids, said feedstock being deflected at the entrance to said another section of said contacting zone sufficiently to move said solids in a generally circumferential and horizontal direction, converting at least part of said feedstock to said product, and removing said product from said another section of said contacting zone; and returning said particulate solids to said one section of said contacting zone. The product can then be converted to higher order hydrocarbons, especially substantially liquid hydrocarbons.

BRIEF DESCRIPTION OF THE DRAWINGS

In the annexed drawings, like references indicate like parts or features.

DESCRIPTION OF THE PREFERRED EMBODIMENTS

Figure 1:
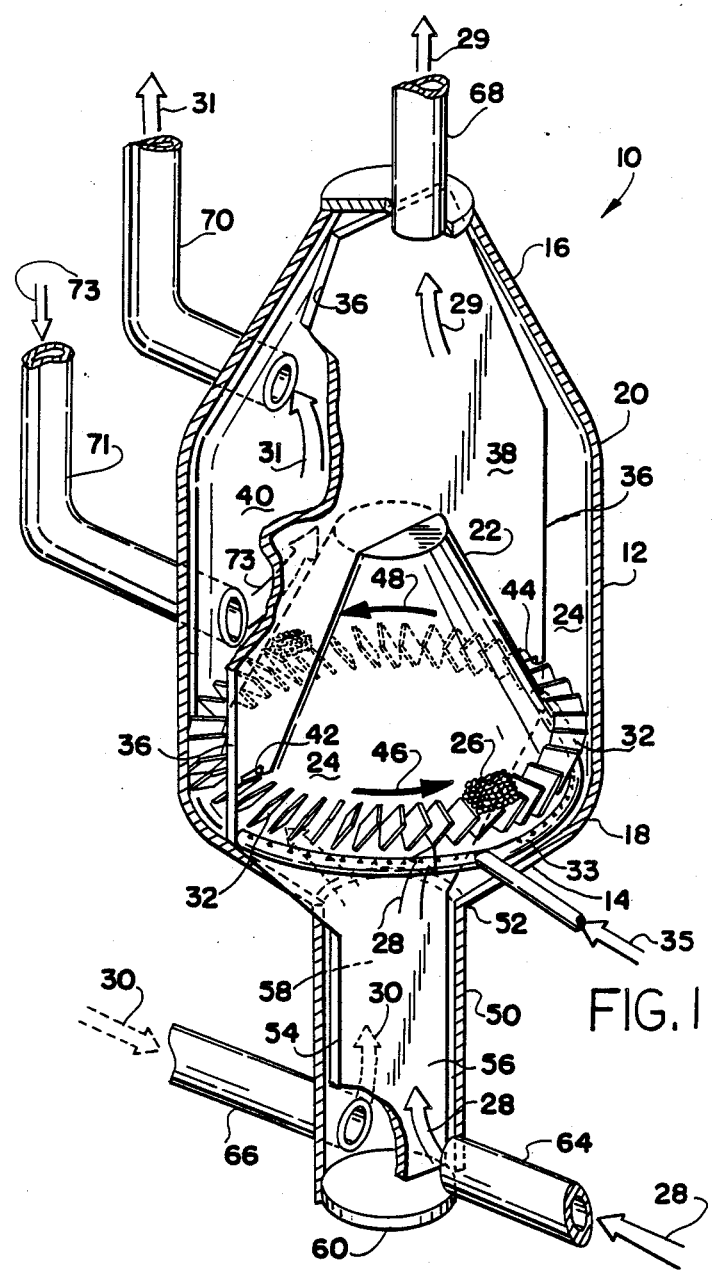
FIG. 1 is a partially cut-away, perspective view illustrating a gas-solids contactor for conducting the inventive process in a particular manner.

Apparatus:

Referring initially to FIG. 1, a gas-solids contactor for heating particulate solids in one section of said contactor and contacting a feedstock with said solids in another section of said contactor is indicated generally by the reference numeral 10. Contactor 10 comprises a vertical cylindrical member 12, a lower frustoconical member 14 and an upper frustoconical member 16. The lower frustoconical member 14 is co-axial with and depends from vertical cylindrical member 12. Frustoconical member 14 has its base formed integrally with the lower end of cylindrical member 12 at the junction indicated by the reference numeral 18. Alternatively, frustoconical member 14 can be bolted or welded to cylindrical member 12 or otherwise mounted in any suitable manner. The upper frustoconical member 16 is also co-axial with the cylindrical member 12 and has its base formed integrally with the upper end of cylindrical member 12 at the junction indicated by the reference numeral 20. Alternatively, frustoconical member 16 can be bolted or welded to cylindrical member 12 or otherwise mounted in any suitable manner.

A vertically extending interior frustoconical member 22 is mounted within cylindrical member 12. Interior frustoconical member 22 is co-axial with cylindrical member 12. The annular space 24 between cylindrical member 12 and interior frustoconical member 22 comprises a contacting zone for contacting a bed of particulate solids 26 with separate gaseous or vaporized streams, one of which is a mixture of gaseous or vaporized stream 28 and gaseous or vaporized fuel 35 and the other is gaseous or vaporized stream 30. An array of evenly spaced overlapping angled blades 32 is disposed across the entrance to annular space 24 between cylindrical member 12 and interior frustoconical member 22. A semi-circular sparging ring 33 is positioned below or downstream of angled blades 32 and is adopted for advancing fuel 35 into contactor 10 and mixing it with stream 28.

Planar member 36 is mounted in the interior space defined by cylindrical member 12, lower frustoconical member 14 and upper frustoconical member 16. Planar member 36 divides said interior space into two separate sections 38 and 40. Planar member 36 includes openings or passageways 42 and 44 just above blades 32 to permit particulate solids 26 to pass between interior sections 38 and 40. That is, during operation of the inventive process (as described in greater detail below) particulate solids 26 are entrained by streams 28 and 30 and move in a generally circumferential direction, as indicated by directional arrows 46 and 48, through contacting zone 24 in a plane just above angled blades 32, and in doing so pass through passageways 42 and 44 from interior section 38 to interior section 40 and then back again.

Depending from lower frustoconical member 14 is lower vertically extending cylindrical member 50. Cylindrical member 50 can be formed integrally with the lower converging end 52 of lower frustoconical member 14. Alternatively, cylindrical member 50 can be bolted or welded to the lower convergent end 52 of frustoconical member 14, or otherwise attached in any suitable manner. Planar member 54 is mounted in the interior of cylindrical member 50 and divides the interior space defined by cylindrical member 50 into separate vertically extending sections 56 and 58. Planar member 54 can be formed integrally with or welded to planar member 36, or otherwise attached so as to maintain the interior space defined by interior sections 38 and 56 separate from the interior space defined by interior sections 40 and 58. Plate member or end closure 60 closes off the bottom end of cylindrical member 50.

Conduits 64 and 66 are connected to cylindrical member 50 and are adapted for conveying gaseous or vaporized streams 28 and 30 into interior sections 56 and 58, respectively. Conduits 68 and 70 are connected to upper frustoconical member 16, and are adapted for conveying gaseous or vaporized products 29 and 31 from interior sections 38 and 40, respectively. Conduit 71 is connected to cylindrical member 12 and adapted for conveying a gaseous or vaporized quenching stream 73 into interior section 40.

Catalyst:

The particulate solids 26 can be any catalytic material that is stable under the operating conditions employed and is suitable for enhancing the combustion of the gaseous or vaporized fuel 35. These catalytic materials are sometimes referred to in the art as oxidation catalysts. Preferred catalysts are prepared by dispersing non-noble metals throughout the lattice of a high-refractory or temperature-resistant oxide complex. These preferred catalysts can be represented by the formula

wherein

A is an alkali or alkaline earth metal, preferably Li, Na, K, Rb, Be, Mg, Ca or a mixture of two or more thereof;

M is V, Cr, Mo, Mn, Fe, Co, Ni, Cu or a mixture of two or more thereof, preferably V, Fe or Cr;

D is Zr, Ti, Hf, Ce, Th, Pr, Nb, Ta, W, Re or a mixture of two or more thereof, preferably Zr, Ce or Th;

E is Ca, Mg, Sr, Ba, Y, La, Yb, Sm, Gd, Nd, Sc, V, Bi, Ce, Pr, Eu, Tb, Dy, Ho, Er, Tm, Lu or a mixture of two or more thereof, preferably Ca, Mg, Y or La;

a is a number in the range of zero up to about 0.2, preferably about 0.05 to about 0.08;

w is the number of oxygens needed to fulfill the valence requirements of AM;

x is the number of oxygens needed to fulfill the valence requirements of D;

y is the number of oxygens needed to fulfill the valence requirements of E; and z is a number in the range of about 10 to about 100, preferably about 15 to about 30.

In the above formula the complex within the brackets "[]" represents the lattice structure. A functions primarily as a catalytic modifier. M is a catalytically active metal. D functions primarily as a refractory metal; it is chosen to provide a high temperature and attrition-resistant oxide complex. E is a stabilizing element. The value of z is chosen to insure that the catalyst is a high refractory or high-temperature resistant material.

With these preferred catalysts, the most abundant metallic element is D, hence the physical properties of these catalysts are similar to those of $DO_x$-type materials. Since element D is chosen to form a high-temperature and attrition-resistant oxide, the preferred catalysts are highly resistant to attrition and high-temperature degradation. They exhibit longer useful lifetimes under routine combustion conditions than catalysts suggested in the prior art.

These preferred catalysts can be prepared by dissolving a salt or sol of the refractory metal oxide, $DO_x$, in water (or other appropriate solvent) and introducing soluble species or slurries of reagents that contain the stabilizing element E, the catalytically active element M and the modifying element A. Salts that are suitable include nitrates, acetates, halides, carbonates, sulphates, phosphates, tartrates, alkoxides, hydrated oxides, and the like. The mixture is heated until the water or other solvent is driven off. The dried mixture is then heat treated at temperature up to about 1500° C., preferably about 700° C. to about 900° C., for about 1 to about 24 hours. Alternately, the refractory oxide stabilizing element lattice is preformed and then impregnated with the catalytically active element and modifying element and fired at a temperature up to about 1500° C., preferably about 700° C. to about 900° C.

In order to further illustrate the preparation of these preferred catalysts, the following examples are provided. In the following examples as well as throughout the specification and in the appended claims, all parts and percentages are by weight and all temperatures are in degrees centigrade, unless otherwise indicated.

EXAMPLE 1

A catalyst of composition $VZr_{30}O_{62.5}$ was prepared in the following manner: 36.97 gms. of $ZrO_2$ were slurried in 200 ml. of water. 1.17 gms. of $NH_4VO_3$ were added to this slurry and the pH was adjusted to 12 by the addition of a concentrated $NH_3$ solution. This slurry was heated at reflux for 16 hours then evaporated to near dryness. The catalyst was heat treated in air at 120° C. for 16 hours.

EXAMPLE 2

A calcium stabilized catalyst of a similar composition to that in Example 1 was prepared as follows: 36.97 gms. of Ca stabilized $ZrO_2$ were slurried in 200 ml. of water 1.17 gms. of $NH_4VO_3$ were added to this slurry and the pH was adjusted to 12 by the addition of a concentrated $NH_3$ solution. This slurry was heated at reflux for 18 hours then evaporated to near dryness. The catalyst was heat treated in air at 120° C. for 16 hours.

EXAMPLE 3

A catalyst of composition $CrZr_{30}O_{61.5}$ was prepared in the following manner: 37.0 gms. of $ZrO_2$ were slurried in 200 ml. of water. 4.0 gms. of $Cr(NO_3)_3.9H_2O$ were added to this slurry. This slurry was heated at reflux for 16 hours then evaporated to near dryness. The catalyst was heat treated in air at 120° C. for 16 hours.

EXAMPLE 4

A catalyst of composition $CrZr_{30}O_{61.5}$ and also containing Ca to stabilize the the cubic form of zirconia at room temperature was prepared in the following manner: 37.0 gms. of $ZrO_2$ were slurried in 200 ml. of water. 4.0 gms. of $Cr(NO_3)_3.9H_2O$ were added to this slurry. This slurry was heated at reflux for 16 hours then evaporated to near dryness. The catalyst was heat treated in air at 120° C. for 16 hours.

EXAMPLE 5

A catalyst of composition $FeZr_{30}O_x$ was prepared in the following manner: 37.0 grams of $ZrO_2$ were slurried in 200 ml of water. 4.0 grams of $Fe(NO_3)_3.9H_2O$ were added, and the mixture was heated at reflux for 16 hours. The mixture was evaporated to near dryness, then dried at 120° C. for 16 hours. The catalyst was calcined at 290° C. and 425° C. for 3 hours each, then heated at 900° C. for 16 hours. The resulting catalyst was then ground to 20–35 mesh.

Process:

The inventive process involves converting a gaseous or vaporized hydrocarbon feedstock to a product comprising ethylene, acetylene or a mixture thereof using the gas-solids contactor 10. The gaseous or vaporized stream 30 is the feedstock. The gaseous or vaporized stream 28 is an oxygen source. Stream 28 advances through conduit 64 into interior section 56. Gaseous or vaporized fuel 35 enters interior section 56 through sparging ring 33 and mixes with gaseous or vaporized stream 28. The mixture of stream 28 and fuel 35 advances upwardly through interior section 56 into contact with angled blades 32 in interior section 38. Upon contacting blades 32, a horizontal component is introduced into the direction of flow of the mixture of stream 28 and fuel 35. The mixture of stream 28 and fuel 35 passes between blades 32 and into contact with particulate solids 26 which are in the form of a bed of particulate solids and are at an elevated temperature. This elevated temperature, which is preferably in the range of about 800° C. to about 1700° C. as discussed below, is achieved at start-up using conventional techniques (e.g., heating the solids prior to placing them in contactor 10). After start-up, this elevated temperature is maintained by the combustion of fuel 35 and to the continuous circulation of solids 26 as discussed below. The flow of stream 28 and fuel 35 through solids 26 induces a substantially horizontal and circumferential direction to the movement of solids 26 in the direction indicated by directional arrows 46 and 48 in a plane just above blades 32. As stream 28 and fuel 35 pass through solids 26 they are heated by solids 26 sufficiently for fuel 35 to undergo a combustion reaction with stream 28. Combustion preferably occurs in the bed of solids 26 resulting in the heating of said solids. Exhaust gases or vapors from the combustion and unreacted gases or vapors advance upwardly from solids 26 as gaseous or vaporous material 29 through interior section 38 to and through conduit 68 from which they are removed from gas-solids contactor 10. The velocity of fuel 35 is preferably maintained at a higher rate than its flame propogation velocity to prevent the flames from backing below the bed of solids 26. The heated solids 26 are advanced through passageway 44 into interior section 40.

Feedstock 30 advances through conduit 66 into interior section 58. In interior section 58 feedstock 30 and stream 28 are separated by planar member 54. Feedstock 30 advances upwardly through interior section 58 into contact with angled blades 32 in interior section 40 where it is deflected horizontally. Feedstock 30 passes between blades 32 into contact with heated solids 26. The contacting of solids 26 with feedstock 30 induces a substantially horizontal and circumferential direction to the movement of solids 26 in the direction indicated by directional arrows 46 and 48 in a horizontal plane just above blades 32. Feedstock 30 passes through solids 26 and undergoes a conversion reaction resulting in the formation of product gases or vapors 31 comprising ethylene, acetylene or a mixture thereof. The nature of this conversion reaction is dependent upon the particular feedstock employed. While not wishing to be bound by the theory, it is believed that methane undergoes a pyrolysis reaction while higher order hydrocarbons (i.e., $C_{2}+$ hydrocarbons) undergo thermal cracking. The product gases or vapors 31 advance upwardly from solids 26 through interior section 40. A gaseous or vaporized quenching stream 73 advances into interior section 40 through conduit 71, and contacts and cools product gases or vapors 31 to a desired temperature (preferably below about 400° C.) to terminate or substantially terminate further reaction of the product gases or vapors 31 before they leave interior section 40. The solids 26 advance through passageway 42 back into interior section 38 where the cycle starts again. Carbon build-up that occurs on the solids 26 during the conversion reaction in interior section 40 is burned off during combustion in interior section 38. Dead spots with slightly different elevations are preferably used at passageways 42 and 44 to minimize gas leakage between the two interior sections 38 and 40. Also, a slightly higher operating pressure in one of the interior sections 38 or 40 can be used to prevent gas leakage into such section.

Figure 2:
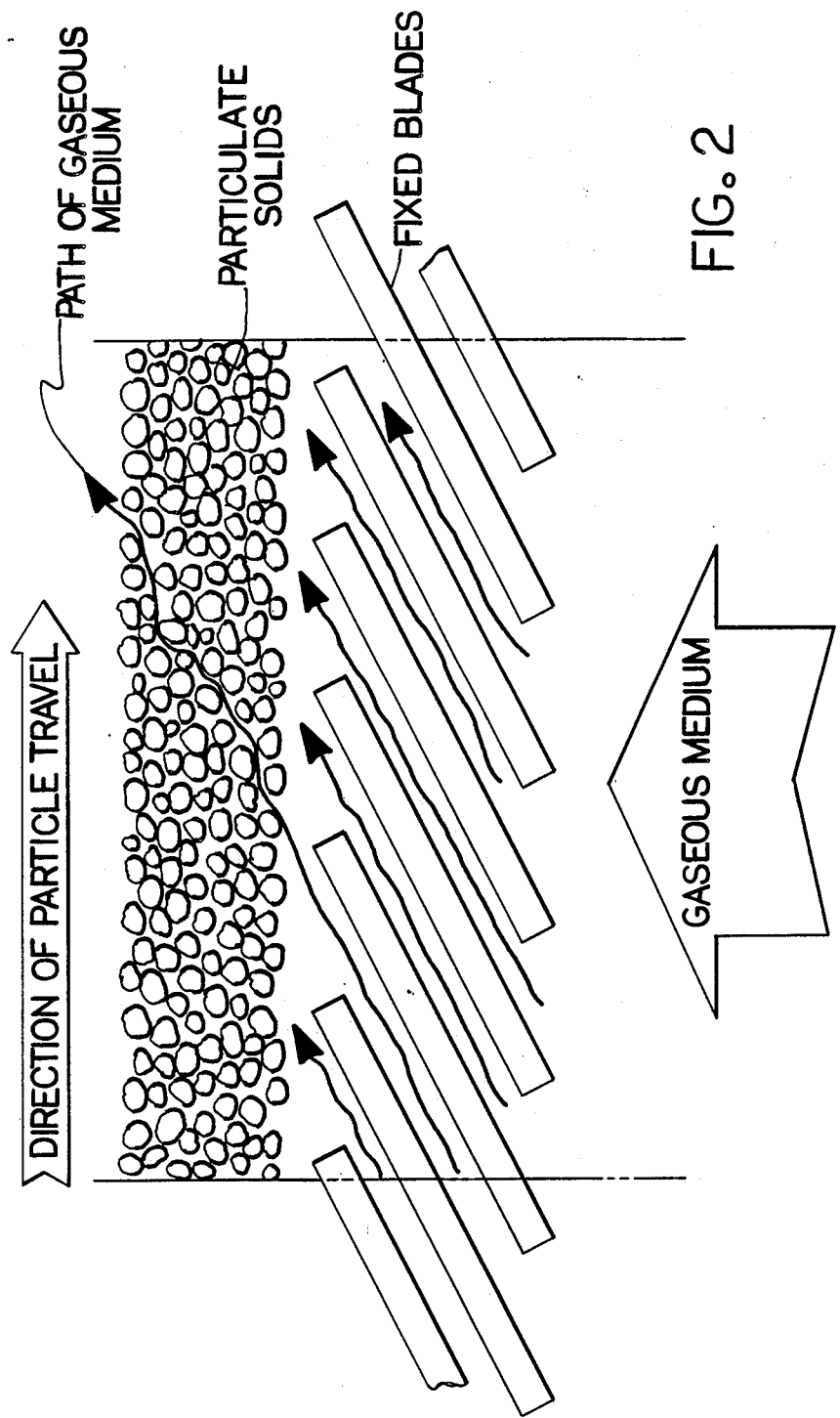
FIG. 2 is a schematic illustration illustrating the contacting of particulate catalytic solids with a gaseous or vaporized stream in accordance with the inventive process.

The contacting of particulate solids 26 with the mixture of gaseous or vaporized stream 28 and gaseous or vaporized fuel 35, and gaseous or vaporized feedstock 30 is illustrated in greater detail in FIG. 2. The gaseous medium (i.e., the mixture of stream 28 and fuel 35, or feedstock 30) advances upwardly into contact with the fixed blades (i.e., fixed blades 32) and is deflected to provide the gaseous medium with a horizontal component to its direction of flow. As the gaseous medium passes through the bed of particulate solids (i.e., particulate solids 26), it moves such solids in a generally circumferential and horizontal direction. The particulate solids are floated or flown in a horizontal plane just above the fixed blades. The velocity of the gaseous medium as it passes through the fixed blades and contacts the lower layer of the bed of particulate solids is generally relatively high, but such velocity is dissipated as it passes through the bed of solids. The dissipation of the gaseous velocity as it passes through the bed of particulate solids enables the use of relatively high gaseous velocities and, consequently, relatively high heat transfer and/or mass transfer rates, without causing significant entrainment of the particulate solids out of contactor 10.

The gaseous or vaporized stream 28 is an oxygen source. Gaseous or vaporized stream 28 is preferably air but can be substantially pure oxygen or oxygen diluted with nitrogen, carbon dioxide, carbon monoxide, or other inert gases (e.g., noble gases such as helium, neon, argon, etc.) The molar ratio of oxygen in stream 28 to fuel 35 is preferably in the range of about 0.1 to about 10, more preferably from about 0.2 to about 5. The volumetric ratio of gaseous or vaporized stream 28 to gaseous or vaporized fuel 35 is preferably from about 0.4 to about 40, more preferably from about 0.8 to about 20.

The gaseous or vaporized fuel 35 can be any gaseous or vaporized fuel normally used for combustion. Examples of such fuels include natural gas, hydrocarbons containing from about 1 to about 5 carbon atoms, (e.g., methane, ethane, ethylene, acetylene, propane, propylene, the butanes, the butylenes, the pentanes, the pentylenes), liquid petroleum gas (LPG), and the like, as well as mixtures of two or more of these. Mixtures of these fuels with hydrogen can also be used.

The natural gas can be either wellhead natural gas or processed natural gas. Wellhead natural gas typically contains about 40% to about 95% methane, depending on the particular source; other constituents typically include about 10% ethane with the balance being made up of carbon dioxide and smaller amounts of propane, the butanes, the pentanes, nitrogen, etc. Prior to commercial use, wellhead natural gas is typically processed to remove water vapor, condensible hydrocarbons and inert or poisonous constituents. Condensible hydrocarbons are generally removed by cooling natural gas to a low temperature and then washing the natural gas with a cold hydrocarbon liquid to absorb the condensible hydrocarbons. The condensible hydrocarbons are typically ethane and heavier hydrocarbons. This gas processing can occur at the wellhead or at a central processing station. The composition of processed natural gas varies with the needs of the ultimate user. Processed natural gas typically comprises a major amount of methane, and minor amounts of ethane, propane, the butanes, the pentanes, carbon dioxide and nitrogen. Generally, processed natural gas comprises from about 70% to more than about 95% by volume of methane.

The gaseous or vaporized hydrocarbon feedstock 30 preferably comprises methane, ethane, propane, butane, natural gas, and/or at least one heavy hydrocarbon that is a liquid or substantially liquid at 20° C. and a pressure of one atmosphere and has a boiling point in the range of about 30° C. and about 600° C. The natural gas can be either wellhead natural gas or processed natural gas, as discussed above. Useful heavy hydrocarbons include naphtha with a boiling point in the range of about 30° C. to about 170° C., atmospheric gas oil (AGO) with a boiling point in the range of about 230° C. to about 330° C., and vacuum gas oil with a boiling point in the range of about 300° C. to about 540° C. The feedstock may include minor amounts of additional hydrocarbons, typically containing from 2 to about 5 carbon atoms. These hydrocarbons include, for example, ethylene, acetylene, propylene, the butylenes, the pentanes, the pentylenes, and the like as well as mixtures of two or more of said hydrocarbons. Hydrogen and/or diluents can be mixed with the feedstock. Examples of such diluents include steam, nitrogen, carbon dioxide, carbon monoxide, and other inert gases (e.g., noble gases such as helium, neon, argon, etc.). The feedstock preferably contains at least about 50% by volume hydrocarbon, more preferably from about 50% to about 95% by volume hydrocarbon. The feedstock can contain from zero up to about 25 moles of hydrogen and/or diluents per mole of hydrocarbon. The feedstock can also contain from zero up to about 25 moles of water per mole of hydrocarbon.

In interior section 38, the particulate solids 26 are preferably heated to an average temperature in the range of about 800° C. to about 1700° C., more preferably in the range of about 1000° C. to about 1600° C., more preferably about 1200° C. to about 1600° C. The solids 26 are then advanced to interior section 40 wherein they are contacted with the feedstock to effect the conversion reaction. The conversion reaction preferably occurs at an average temperature in the range of about 800° C. to about 1700° C., more preferably about 1000° C. to about 1600° C., more preferably about 1200° C. to about 1400° C. The gaseous or vaporized quenching stream 73, which can be natural gas, water, steam or any other suitable process stream or material, preferably contacts and mixes with the product gases or vapors 31 at a point just above the bed of solids 26 for an effective period of time to reduce the temperature of the resulting gaseous or vaporous mixture (i.e., gaseous or vaporizes products 31 and gaseous or vaporized quenching stream 73) to a temperature below about 400° C. to terminate or substantially terminate further reaction. By controlling the conversion reaction time in this manner, the overall composition of the product gases or vapors 31 can be controlled.

The conversion reaction can be conducted at subatmospheric, atmospheric or at elevated pressures up to about 5 atmospheres. Generally, the reaction is conducted at a pressure of from about 0.5 to about 2 atmospheres, and more preferably about 1 to about 1.5 atmospheres.

The particulate solids 26 preferably have average diameters in the range of about 0.01 mm to about 12 mm, more preferably from about 0.1 mm to about 6 mm. The bed of particulate solids 26 is preferably from about 10 mm to about 100 mm deep in the vertical plane, more preferably from about 20 mm to about 60 mm deep. The average velocity of the mixture of gaseous or vaporous stream 28 and gaseous or vaporous fuel 35, and feedstock 30 upon contacting the lower layer of the bed of particulate solids 26 is preferably in the range of about 5 to about 75 meters per second, more preferably from about 10 to about 50 meters per second. The average velocity of each of the product gases or vapors 29 and 31 at the upper surface of the bed of particulate solids 26 is preferably in the range of about 0.1 to about 10 meters per second, more preferably in the range of about 0.5 to about 5 meters per second. The average residence time of the mixture of stream 28 and fuel 35 in the bed of particulate solids 26 in interior section 38 is preferably in the range of about 1 to about 1000 milliseconds, more preferably about 1 to about 400 milliseconds, more preferably about 5 to about 100 milliseconds, more preferably about 10 to about 50 milliseconds. The average residence time of the feedstock 30 within the bed of particulate solids 26 is generally a time which is sufficient to provide the desired conversion. However, the residence time should not be so long as to provide sufficient time for the products obtained to decompose to carbon. Accordingly, a residence time preferably in the range of from about 1 to about 1000 milliseconds, more preferably about 1 to about 400 milliseconds is useful, and residence times in the range of about 5 to about 150 milliseconds, preferably about 5 to about 100 milliseconds are generally preferred. Residence times of about 10 to about 50 milliseconds are useful.

The overall composition of the product produced in accordance with this inventive process may vary somewhat depending upon the nature or source of the feedstock that is initially used and the conditions under which it is processed. This product typically comprises mixtures of hydrocarbons containing at least some ethylene and/or acetylene. Preferably, this product contains up to about 90% by volume acetylene, more preferably from about 30% to about 80% by volume acetylene; and up to about 90% by volume ethylene, more preferably from about 30% to about 50% by volume ethylene. The product can further comprise hydrogen. Hydrogen is preferably present in such product at a level of up to about 90% by volume, more preferably at a level in the range of about 10% to about 80% by volume.

In one embodiment of the invention, this product can comprise from about 1% to about 90% by volume ethylene, more preferably from about 10% to about 40% by volume ethylene; from about 1% to about 90% by volume acetylene, more preferably from about 20% to about 70% by volume acetylene; and from about 1% to about 90% by volume hydrogen, more preferably from about 10% to about 80% by volume hydrogen.

In addition to ethylene and/or acetylene, and optionally hydrogen, this product can further comprise light hydrocarbons, (e.g., methane, ethane, propane, propylene, and the like), natural gas and/or heavier hydrocarbons (e.g., hydrocarbons having a boiling point in the range of about 30° C. to about 600° C.).

The product can be diluted with carbon dioxide and/or carbon monoxide. It can also be diluted with nitrogen and other inert gases (e.g., noble gases such as helium, neon, argon, etc.). The mole ratio of carbon dioxide, carbon monoxide and/or inert gases to hydrocarbon in the product can range from zero up to about 25 moles each per mole of hydrocarbon, but is preferably less than about 10, more preferably less than about 3 moles of each per mole of hydrocarbon.

Figure 3:
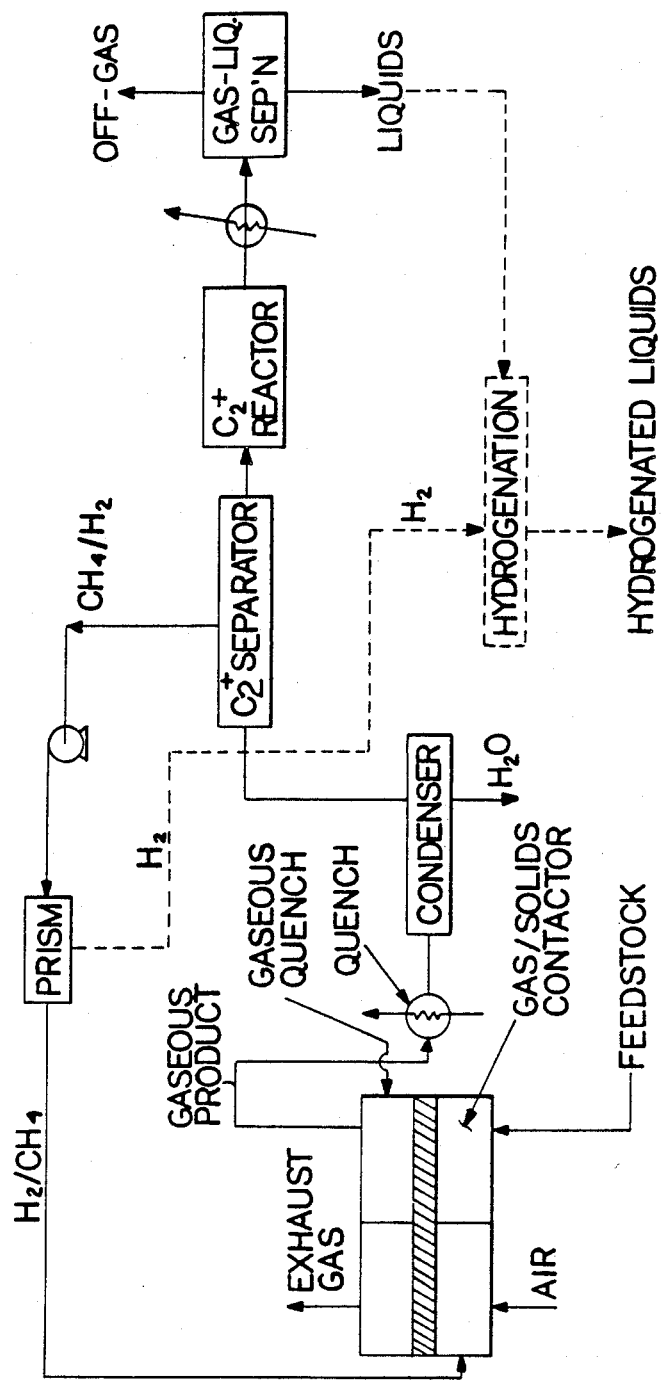
FIG. 3 is a flow sheet illustrating the process of the invention for converting a gaseous or vaporized hydrocarbon feedstock to a product comprising ethylene, acetylene or a mixture thereof, and then converting the product to higher order hydrocarbons.

A preferred technique for operating the inventive process to convert a gaseous or vaporized hydrocarbon feedstock to a product comprising ethylene and/or acetylene, and to then convert said product to higher order hydrocarbons, especially liquid hydrocarbons, is illustrated in FIG. 3. The gas-solids contactor indicated in FIG. 3 is the contactor 10 illustrated in FIG. 1. Referring to FIGS. 1 and 3, the feedstock 30 is preheated to a temperature that is preferably in the range of about 200° C. to about 700° C. and then is advanced through conduit 66 into interior section 58 of contactor 10. Feedstock 30 advances upwardly through interior section 58, is deflected by angled blades 32, contacts particulate solids 26 and undergoes a conversion reaction at a temperature in the range of about 800° C. to about 1700° C. to form a gaseous or vaporized product 31 comprising ethylene, acetylene or a mixture thereof. The product 31 is quenched to a temperature sufficiently low enough (preferably below about 400° C.) to terminate or substantially terminate further reaction by mixing it with gaseous or vaporous quenching stream 73 in interior section 40, preferably just above the bed of particulate solids 26. The product 31 is then advanced upwardly through interior section 40 to and through conduit 70.

The gaseous or vaporized stream 28 (e.g., air) is preheated to a temperature that is preferably in the range of about 200° C. to about 700° C., enters gas-solids range of about 200° C. to about 70 contactor 10 through conduit 64, and advances through conduit 64 into interior section 56. Stream 28 advances upwardly through interior section 56 where it is mixed with gaseous or vaporized fuel 35 (e.g., $H_2/CH_4$) which enters contactor 10 through sparging ring 33. The mixture of stream 28 and fuel 35 advances upwardly through interior section 56 where it is deflected by angled blades 32 and then contacts particulate solids 26. Combustion of the gaseous fuel 35 takes place in the bed of particulate solids 26. The gaseous or vaporous by-products of combustion (i.e., exhaust gases) and non-combusted or non-reacted gases or vapors are removed from the gas-solids contactor 10 as gaseous or vaporous stream 29 through conduit 68.

The velocity of the feedstock 30 and the mixture of stream 28 and fuel 35 through the bed of particulate solids 26 is sufficient to move the solids 26 circumferentially from interior section 38 to interior section 40, and then back again on a continuous basis.

The product 31 is advanced from the gas-solids contactor 10 to a water or solid quench to quench the gaseous or vaporized products at a temperature that is preferably in the range of about 10° C. to about 700° C., more preferably in the range of about 10° C. to about 100° C. The quenched products are then advanced to a condenser wherein water is removed. From the condenser, the products are advanced to a $C_2+$ separator wherein gaseous or vaporized fuel (i.e., $CH_4/H_2$) is separated. The higher order hydrocarbon products (i.e., $C_2+$ hydrocarbon products) are then advanced to a $C_2+$ reactor (e.g., fluid bed, trickle bed or fixed bed) for conducting low temperature pyrolysis (i.e., pyrolysis at a temperature in the range of about 400° C. to about 900° C.). The exothermic heat from this low-temperature pyrolysis reaction can be used to preheat the gaseous or vaporized feedstreams entering the gas-solids contactor. The products from this low-temperature pyrolysis reactor are advanced to a gas-liquid separator wherein the gaseous products are separated from the liquid products. In an optional step, the liquid products can be hydrogenated. The gaseous fuel that is separated from the higher order hydrocarbon products in the $C_2+$ separator can be recycled back to the gas-solids contactor. Hydrogen can be separated from this recycled gaseous fuel using a prism separator; the separated hydrogen can be used to hydrogenate the liquid hydrocarbon products.

Optionally, the $C_2+$ hydrocarbon conversion to liquid hydrocarbon products can be conducted without separation of the $C_2+$ hydrocarbons in a $C_2+$ separator. To do this the product stream 31 is quenched to an intermediate temperature, preferably in the range of about 500° C. to about 1000° C. This intermediate quenching step results in the $C_2+$ hydrocarbons reacting autothermally to produce the liquid hydrocarbon products. The time period for this intermediate quenching is preferably from about 50 to about 400 milliseconds. A fluid bed may be used in this quenching step to maintain isothermal conditions. Cooling coils may also be used to remove process heat. The product stream is then quenched externally and advanced to the gas-liquid separation unit. The hydrogen and unconverted hydrocarbons are recovered from this unit.

Since the process of the present invention is well-suited to a continuous, cyclic process, the lighter weight gaseous hydrocarbon products such as ethane or propane, etc. can be separated from the more desirable higher molecular weight liquid hydrocarbon products and recycled in the process for further conversion to higher molecular weight liquid hydrocarbon products. Unsaturated hydrocarbons such as ethylene, acetylene, propene, etc., may be present in the gaseous hydrocarbon products obtained in this invention and these may be recycled through the process for conversion to higher molecular weight liquid products and/or as added initiators for the conversion of fresh feedstock to liquid products.

Preferred higher order hydrocarbon products made by the process of the present invention are aliphatic and/or aromatic products that are sufficiently liquid to be readily handleable and transportable in conventional pipeline systems. Included in this preferred group are hydrocarbons containing at least about 5 carbon atoms, more particularly, aromatic compounds containing at least 6 carbon atoms.

The inventive process has a number of significant advantages. The feedstock can be heated to a relatively high temperature (e.g., 1700° C.) very rapidly (e.g., 1–1000 milliseconds, preferably 1–400 milliseconds, and, preferably below about 150 milliseconds). By using the catalytic solids 26 complete combustion of the gaseous fuel can be achieved in a relatively short period of time (e.g., 1–1000 milliseconds, 1–400 milliseconds, etc.). The particulate solids 26 do not circulate from one vessel to another, or from one ring to another. Any carbon formed during the conversion of feedstock in interior section 40 is burned off in interior section 38 of the contactor 10. Proven materials of construction for the contactor 10 can be used. The temperature of the angled blades 32 can be kept to a minimum by using in-bed combustion (i.e., combustion in the bed of particulate solids 26 above blades 32). Preheated gaseous or vaporized fuel or preheated mixtures of gaseous or vaporized fuel and air, and preheated feedstocks can be passed through the angled blades 32. Due to relatively high circulation velocities (i.e., from about 0.5 to about 2 meters per second) of the particulate solids 26 that can be used, the temperature gradients in the bed of particulate solids 26 can be kept to a minimum (e.g., about 20° C.). The contactor vessel 10 can be very compact and thus large gaseous through-puts can be achieved in a very small contactor vessel volume.

While the invention has been explained in relation to its preferred embodiments, it is to be understood that various modifications thereof will become apparent to those skilled in the art upon reading this specification. Therefore, it is to be understood that the invention disclosed herein is intended to cover such modifications as fall within the scope of the appended claims.

We claim:

1. A process for converting a gaseous or vaporized hydrocarbon feedstock to a product comprising ethylene, acetylene or a mixture thereof, the process comprising:

advancing a gaseous or vaporous stream comprising a gaseous or vaporous fuel and an oxygen source into contact with particulate solids in one section of an annular gas-solids contacting zone, said stream being deflected at the entrance to said one section of said contacting zone sufficiently to move said solids in a generally circumferential and horizontal direction, said particulate solids being at a sufficiently high temperature to effect combustion of said fuel, said particulate solids comprising an effective amount of at least one oxidation catalyst to enhance the combustion of said fuel, combusting said fuel, the heat from said combustion heating said solid and removing a gaseous or vaporous material comprising exhaust gases or vapor from said combustion from said one section of said contacting zone;

moving said particulate solids to another section of said contacting zone to effect contact between said solids and said feedstock, the movement of said solids being effected by the flow of said gaseous stream;

advancing said feedstock into said another section of said annular contacting zone into contact with said particulate solids, said feedstock being deflected at the entrance to said another section of said contacting zone sufficiently to move said solids in a generally circumferential and horizontal direction, converting at least part of said feedstock to said product, and removing said product from said another section of said contacting zone; and returning said particulate solids to said one section of said contacting zone.

2. The process of claim 1 wherein said oxygen source is preheated to a temperature in the range of about 200° C. to about 700° C. prior to advancing said oxygen source into contact with said particulate solids.

3. The process of claim 1 wherein said feedstock is preheated to a temperature in the range of about 200° C. to about 700° C. prior to advancing said feedstock into contact with said particulate solids.

4. The process of claim 1 wherein said particulate solids are heated to an average temperature in the range of about 800° C. to about 1700° C. in said one section of said contacting zone.

5. The process of claim 1 wherein said feedstock is heated to an average temperature in the range of about 800° C. to about 1700° C. in said another section of said contacting zone.

6. The process of claim 1 wherein said particulate solids have an average diameter in the range of about 0.01 to about 12 mm.

7. The process of claim 1 wherein said particulate solids are in the form of a bed of solids having an average depth of from about 10 mm. to about 100 mm. in the vertical plane.

8. The process of claim 1 wherein said particulate solids are in the form of a bed of solids having a lower layer and an upper surface, the average velocity of said gaseous or vaporous stream upon contacting the lower layer of said bed of particulate solids is in the range of about 5 to about 75 meters per second.

9. The process of claim 1 wherein said particulate solids are in the form of a bed of solids having a lower layer and an upper surface, the average velocity of said gaseous material in said one section of said contacting zone at the upper surface of said bed of particulate solids is in the range of about 0.1 to about 10 meters per second.

10. The process of claim 1 wherein said particulate solids are in the form of a bed of solids having a lower layer and an upper surface, the average velocity of said feedstock upon contacting the lower layer of said bed of particulate solids is in the range of about 5 to about 75 meters per second.

11. The process of claim 1 wherein said particulate solids are in the form of a bed of solids having a lower layer and an upper surface, the average velocity of said product at the upper surface of said bed of particulate solids in said another section of said contacting zone is in the range of about 0.1 to about 10 meters per second.

12. The process of claim 1 wherein said particulate solids are in the form of a bed of solids, the average residence time of said feedstock in said bed of particulate solids is in the range of about 1 to about 1000 milliseconds.

13. The process of claim 1 wherein said product is contacted with a gaseous or vaporous quenching stream in a space above said another section of said contacting zone for an effective period of time to cool said product to a temperature below about 400° C.

14. The process of claim 1 wherein said feedstock comprises methane, ethane, propane, butane, natural gas, at least one hydrocarbon that is liquid or substantially liquid at atmospheric pressure and 20° C. and has a boiling point in the range of about 30° C. to about 60° C., or a mixture of two or more thereof.

15. The process of claim 1 wherein said feedstock comprises methane or natural gas.

16. The process of claim 1 wherein said feedstock comprises naphtha with a boiling point in the range of about 30° C. to about 170° C., atmospheric gas oil with a boiling point in the range of about 230° C. to about 330° C., vacuum gas oil with a boiling point in the range of about 300° C. to about 540° C., or a mixture of two or more thereof.

17. The process of claim 1 wherein said gaseous or vaporous fuel comprises methane, ethane, ethylene, acetylene, propane, propylene, a butane, a butylene, a pentane, a pentylene, or a mixture of two or more thereof.

18. The process of claim 1 wherein said gaseous fuel comprises natural gas, liquified petroleum gas or a mixture thereof.

19. The process of claim 1 wherein said oxygen source comprises air.

20. The process of claim 1 wherein carbon build-up accumulated on said particulate solids in said another section of said contacting zone is burned off in said one section of said contacting zone.

21. The process of claim 1 wherein said contacting zone is divided into two sections.

22. The process of claim 1 wherein said catalyst comprises a complex represented by the formula

$$AMO_w[(DO_x)(EO_y)a]z$$

wherein

A is an alkali or alkaline earth metal;

M is V, Cr, Mo, Mn, Fe, Co, Ni, Cu or a mixture of two or more thereof;

D is Zr, Ti, Hf, Ce, Th, Pr, Nb, Ta, W, Re or a mixture of two or more thereof;

E is Ca, Mg, Sr, Ba, Y, La, Yb, Sm, Gd, Nd, Sc, V, Bi, Ce, Pr, Eu, Tb, Dy, Ho, Er, Tm, Lu or a mixture of two or more thereof;

a is a number in the range of zero up to about 0.2;

w is the number of oxygens needed to fulfill the valence requirement of AM;

x is the number of oxygens needed to fulfill the valence requirements of D;

y is the number of oxygens needed to fulfill the valence requirements of E; and z is a number in the range of about 10 to about 100.

23. The process of claim 22 wherein A is Li, Na, K, Rb, Be, Mg, Ca or a mixture of two or more thereof.

24. The process of claim 22 wherein M is V, Cr or Fe.

25. The process of claim 22 wherein D is Zr, Ce or Th.

26. The process of claim 22 wherein E is Ca, Mg or Y.

27. The process of claim 22 wherein a is from about 0.05 to about 0.08.

28. The process of claim 22 wherein z is from about 15 to about 30.

29. The process of claim 1 wherein hydrocarbons of two or more carbon atoms are separated from said product, said separated hydrocarbons are converted to a mixture of gaseous hydrocarbon products and liquid hydrocarbon products, and said gaseous hydrocarbon products are separated from said liquid hydrocarbon products.

* * * * *